United States Patent
Vraa et al.

(10) Patent No.: US 6,945,713 B2
(45) Date of Patent: Sep. 20, 2005

(54) SHEET MEDIA PACKAGE HAVING RADIO-FREQUENCY IDENTIFICATION TRANSPONDER

(75) Inventors: Timothy S. Vraa, Rosemount, MN (US); Steven W. Tanamachi, Lauderdale, MN (US); Douglas D. Jensen, Woodbury, MN (US); Leah C. Featherstone, Oakdale, MN (US); Terrence H. Joyce, Lakeville, MN (US); Robert W. Spurr, Rochester, NY (US); Eric J. Donaldson, Saint Paul, MN (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/780,779

(22) Filed: Feb. 18, 2004

(65) Prior Publication Data

US 2004/0184801 A1 Sep. 23, 2004

Related U.S. Application Data

(63) Continuation of application No. 09/664,505, filed on Sep. 18, 2000, now Pat. No. 6,811,079.

(51) Int. Cl.⁷ .............................................. G03B 17/26
(52) U.S. Cl. ....................................... 396/511; 206/455
(58) Field of Search ................................ 206/449, 455, 206/389, 408, 413, 415, 416; 396/511

(56) References Cited

U.S. PATENT DOCUMENTS

| | | |
|---|---|---|
| 4,736,215 A | 4/1988 | Hudspeth et al. |
| 4,960,994 A | 10/1990 | Muller et al. |
| 5,132,724 A | 7/1992 | Lemberger et al. |
| 5,229,585 A | 7/1993 | Lemberger et al. |
| 5,428,659 A | 6/1995 | Renner et al. |
| 5,448,324 A | 9/1995 | Okano et al. |
| 5,473,400 A | 12/1995 | Lemberger et al. |
| 5,475,230 A | 12/1995 | Stumpf et al. |
| 5,765,091 A | 6/1998 | Kovach et al. |
| 5,971,281 A | 10/1999 | Frary et al. |
| 5,973,768 A | 10/1999 | Mazion et al. |
| 6,007,971 A | 12/1999 | Star et al. |
| 6,016,913 A | 1/2000 | Tilton |
| 6,047,257 A | 4/2000 | Dewaele |
| 6,106,166 A * | 8/2000 | Spurr et al. ................. 396/578 |
| 6,173,119 B1 | 1/2001 | Manico et al. |
| 6,217,019 B1 | 4/2001 | Ishiduka et al. |
| 6,227,643 B1 * | 5/2001 | Purcell et al. ................. 347/19 |
| 6,246,466 B1 | 6/2001 | Hirano et al. |
| 6,271,536 B1 | 8/2001 | Buytaert |
| 6,381,416 B2 | 4/2002 | Manico et al. |
| 6,446,208 B1 | 9/2002 | Gujar et al. |
| 6,511,148 B1 | 1/2003 | Colombi et al. |
| 6,527,356 B1 | 3/2003 | Spurr et al. |
| 6,546,210 B1 | 4/2003 | Nakamura |
| 6,598,795 B1 | 7/2003 | Prenn |
| 6,628,316 B1 | 9/2003 | Spurr et al. |
| 6,634,814 B2 | 10/2003 | Spurr et al. |
| 6,710,891 B1 * | 3/2004 | Vraa et al. ................. 358/1.12 |
| 2002/0170973 A1 | 11/2002 | Teraura |
| 2003/0076520 A1 | 4/2003 | Haines et al. |
| 2003/0124471 A1 | 7/2003 | Ishii et al. |

* cited by examiner

*Primary Examiner*—David M. Gray
(74) *Attorney, Agent, or Firm*—Susan L. Parulski

(57) ABSTRACT

Sheet media package system includes a cartridge or other packaging for containing a plurality of sheet media; and a radio-frequency identification transponder which stores relevant digital data associated with the cartridge or other packaging.

21 Claims, 11 Drawing Sheets

SHEET MEDIA PACKAGE HAVING RADIO-FREQUENCY IDENTIFICATION TRANSPONDER

CROSS REFERENCE TO RELATED APPLICATIONS

This application is a continuation of U.S. Ser. No. 9/664,505 filed on Sep. 18, 2000 and issued as U.S. Pat. No 6,811,079, incorporated herein by reference.

FIELD OF THE INVENTION

This invention relates in general to sheet media systems and more particularly to a cartridge or other packaging containing sheet media for use in such sheet media imaging systems, the cartridge or other packaging having a radio-frequency identification transponder associated with it.

BACKGROUND OF THE INVENTION

Sheet media imaging systems include laser imaging systems which produce medical images on photosensitive, sheet film from digital medical images generated by diagnostic imaging systems (MRI, CT, US, PET), computed radiography systems, medical image digitizers, digital or analog medical image archives, direct digital radiography or the like. The sheet film can be packaged in optically opaque packaging which is removed under dark room conditions and loaded into a film supply of a laser imager. Dark room film loading is eliminated by the resealable film cartridge disclosed in U.S. Pat. No. 5,473,400, issued Dec. 5, 1995, inventors Lemberger et al. The disclosed cartridge allows for daylight loading and can be reused and removed from the laser imager. U.S. Pat. No. 5,229,585, issued Jul. 20, 1993, inventors Lemberger et al., discloses a bar code system which uses this resealable cartridge to control a laser imaging system. The cartridge has attached to it an optical bar code with a unique cartridge ID, film size, film type information and film sensitometric information. The laser imager has a bar code scanner which reads information from the bar code as the cartridge is opened. An imager management system controls the laser imager as a function of the input data and the information read from the bar code. A film processor develops the film as a function of film type information read from the bar code. The laser imager stores information relating to film usage of the cartridge.

Although the optical bar code system disclosed in the latter two patents is useful for the purposes for which they were intended, certain limitations are inherent in this technology as follows.

1. The optical bar code has a limited data storage capability.

2. There are a limited number of unique bar codes.

3. The data is fixed and cannot be changed.

4. The bar code must be located on the outside of the cartridge to allow scanning, exposing the bar code to wear and dirt which result in bar code read failures.

5. Film usage information is stored in the image management system of the laser imaging system.

Other technologies for encoding data on a cartridge are also limited. Thus, magnetic encodement allows data to be changed but requires precise contact between a magnetic layer on the cartridge and a magnetic head. Electrical contact with a memory chip mounted on a cartridge also requires precise positioning of the cartridge relative to the read/write device. Both technologies are complex and expensive and are susceptible to wear and degradation.

U.S. Pat. No. 5,428,659, issued Jun. 27, 1995, inventors Renner et al. discloses a device for transferring electrical signals and electric energy to the memory device of a cassette by radio frequency signals by means of a capacitive coupling device. Although the disclosed device is useful for the purpose for which it was intended, it requires precise positioning of the cassette for transfer of data and direct contact between the cartridge and the cartridge receiver.

Reference is made to U.S. Pat. No. 6,710,891, (U.S. Ser. No. 09/664,498) filed on Sep. 18, 2000 entitled SHEET MEDIA SYSTEM et al.; U.S. Patent No. 6,173,119 filed on August 11, 1999, entitled CAMERA HAVING RADIO-FREQUENCY IDENTIFICATION TRANSPONDER, by Manico et al.; U.S. Pat. No. 6,381,416 filed on Aug. 11, 1999, titled FILM UNIT HAVING RADIO-FREQUENCY IDENTIFICATION TRAN PONDER, by Manico et al.; U.S. Pat. No. 6,628,316 filed on Dec. 22, 1 98, entitled PRINTER WITH DONOR AND RECEIVER MEDIA SUPPLY TRAYS EACH ADAPTED TO ALLOW A PRINTER TO SENSE TYPE OF MED THEREIN, AND METHOD OF ASSEMBLING THE PRINTER AND TRAYS by Spurr et al.; and U.S. Pat. No. 6,634,814 filed on Aug. 12, 1998, entitled PRINTER MEDIA SUPPLY SPOOL ADAPTED TO ALLOW THE PRINTER TO SENSE TYPE OF MEDIA, AND METHOD OF ASSEMBLING SAME, by purr et al., all of which are commonly assigned and incorporated herein by reference. Reference is also made to U.S. Pat. No. 5,229,585 (Lemberger), U S. Pat. No. 5,428,659 (Renner), and U.S. Pat. No. 5,971,281 (Frary).

There is thus a need for a sheet media system which uses sheet media packaging having encoded data which has a large data storage, which allows reading of and writing to the data storage, which is resistant to degradation due to dirt, wear and tear, and which is simple and economical to implement.

SUMMARY OF THE INVENTION

According to the present invention, there is provided a solution to the needs discussed above.

According to a feature of the present invention, there is provided a sheet media system comprising, packaging which can be communicated with, with or without physical contact with the transponder, and which stores relevant digital data for holding a plurality of sheet media and a radio-frequency identification transponder associated with said cartridge.

According to another feature of the present invention, there is provided a reusable cartridge for holding a plurality of sheet media and a radio-frequency identification transponder associated with said cartridge.

ADVANTAGEOUS EFFECT OF THE INVENTION

The invention has the following advantages.

1. Sheet media packaging is provided having large encoded data storage.

2. The encoded data storage can be read and written to.

3. Encoded data can be read or written quickly.

4. The RFID system is resistant to degradation due to dirt, wear and tear.

5. The RFID system is simple and economical to implement.

6. The RFID system encodes film usage as well as initial film count.

7. The RFID system can encode information on recycling of the cartridge such as number of times cartridge is recycled, time from last recycling, to prevent bad cartridge from being reused.

DETAILED DESCRIPTION OF THE INVENTION

Figure 1:
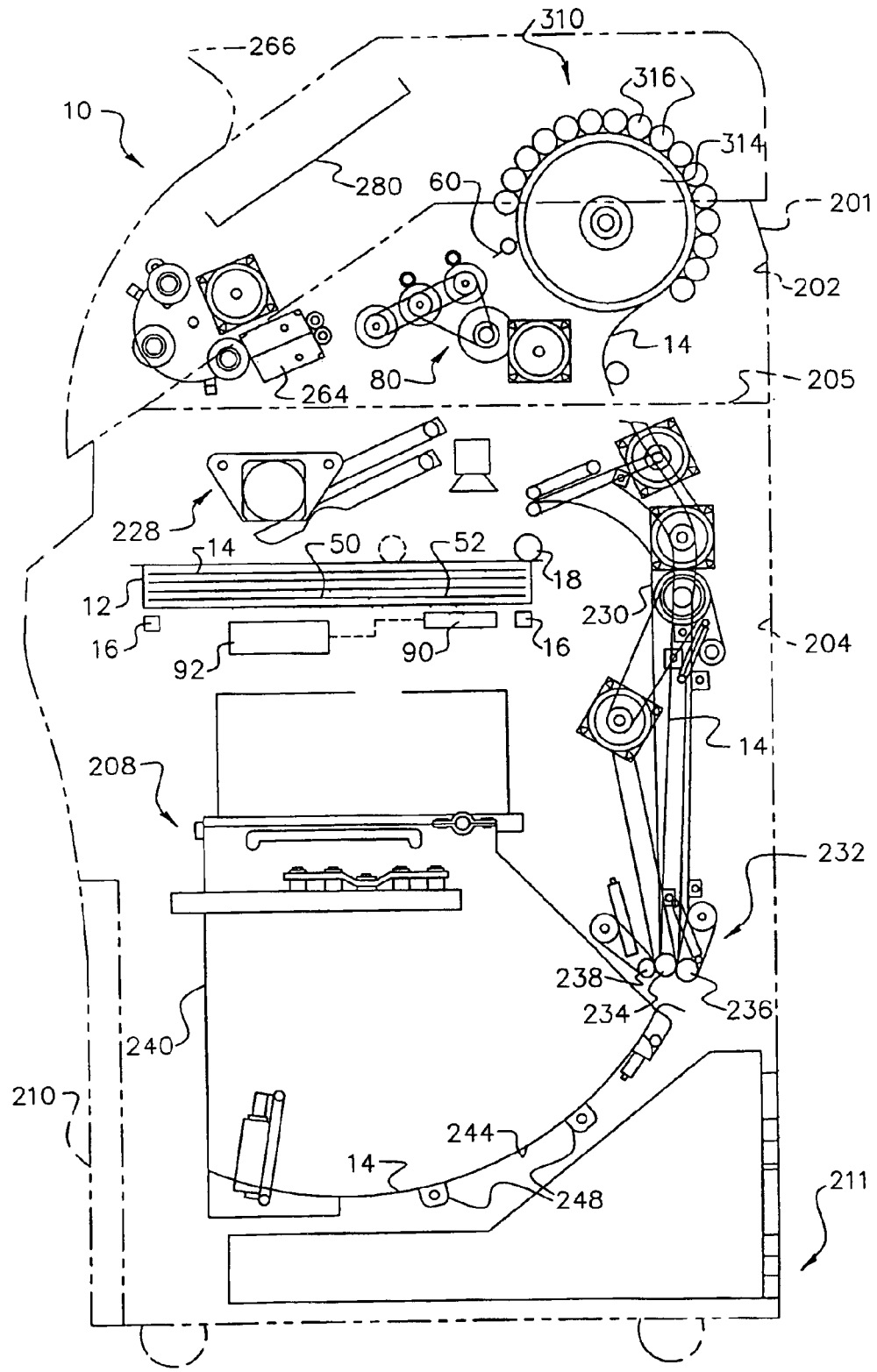
FIG. 1 is a perspective view of a laser imager which uses the present invention.

FIG. 1 shows a sheet media imaging system such as digital imager 10 which is configured to operate with a resealable photographic film cartridge 12. In the embodiment shown, laser imager 10 includes a cartridge-receiving base 16 into which film cartridge 12 with film sheets 14 is loaded. A cartridge opening/closing mechanism 18 is mounted to base 16. Film cartridge 12 is loaded into base 16, and sealed within a light-tight compartment. Opening/closing mechanism 18 then opens cartridge 12 to permit access to film sheets 14 in cartridge 12. Sheets 14 are removed from the opened cartridge 12 and transported to other subsystems of imager 10 (as described below).

Opening/closing mechanism 18 is also actuated to close cartridge 12 before the cartridge is removed from imager 10. Since cartridge 12 is resealable, it can be removed from imager 10 before all the film within the cartridge has been exposed. Cartridges 12 with different sizes or types of film media can therefore be conveniently loaded into and removed from laser imager 10 as needed, without wasting and unused film remaining within the cartridge.

As shown, imager 10 includes an optical scanning module 208, electronics module 210, and integrated thermal processor 310 enclosed in enclosure 201.

Film sheet 14 is transported out of cartridge by suction feed mechanism 228, fed into staging area 230 where sheet 14 is transported by bidirectional film staging mechanism 232 into optical scanning module 208.

Module 208 is mounted onto optical frame 240, for aligning and holding film sheet 14 during the image scanning process. Optical frame 240 is constructed from a rolled sheet metal which is welded to a box-shaped housing. Film sheet 14 transported onto cylindrical film platen 244 where it is scanned.

Film alignment devices 248, align film sheet 14 on platen 244. Once the scanning of the image is complete then exposed film sheet 14 is transported out of film platen 244 toward bidirectional film staging mechanism 232 for transportation of exposed film sheet 14 to thermal processor 310.

Bidirectional film staging mechanism 232 includes a set of three rollers 238, 234, and 236 where center roller 234 is driven and rollers 238, 236 are idlers. Film staging mechanism 232 is designed such that exposed film sheet 14 can be transported out of film platen 244 between rollers 234 and 236 while simultaneously transporting unexposed film sheet 14 onto film platen 244 between rollers 234 and 238, if desired.

Electronics module 210 includes imager control systems. The operator can interface with the electronics through either a keypad mounted on a console, a portable keypad or a modem.

The imager control system receives information from densitometer 264 reads and compares optical density information from an optical density patch generated during the scanning process having a predetermined target optical density on the trailing edge of developed film sheet 14. If necessary, the exposure is adjusted to compensate for any minor differences in optical density.

Enclosure 201 is divided into two primary chambers, upper chamber 202 and lower chamber 204, with a passage for transporting film sheet 14 between the two chambers. Thermal processor 310 is preferably located in upper chamber 202. Lower chamber 204 containing optical scanning module 208, electronics module 210, and power supply 211 and is kept at a positive pressure with respect to upper chamber 202 to prevent damage of the optics due to volatile materials outgassed from film sheet 14 during thermal processing and to protect optical scanning module 208 from detrimental temperature increases. Thermal processor 310 includes rotatable heated member 314 and guiding members 316 for heat development of exposed film sheet 14.

Enclosure 201 can include an openable cover 266. For example, openable cover 266 can be pivotally connected to the remainder of enclosure 201. Guiding members 316 can be attached to cover 266 so that when cover 266 is opened, guiding members 316 are lifted away from heated member 314 providing easier access to heated member 314. After processing, developed film sheet 14 is cooled and deposited in output tray 280.

Figure 2:
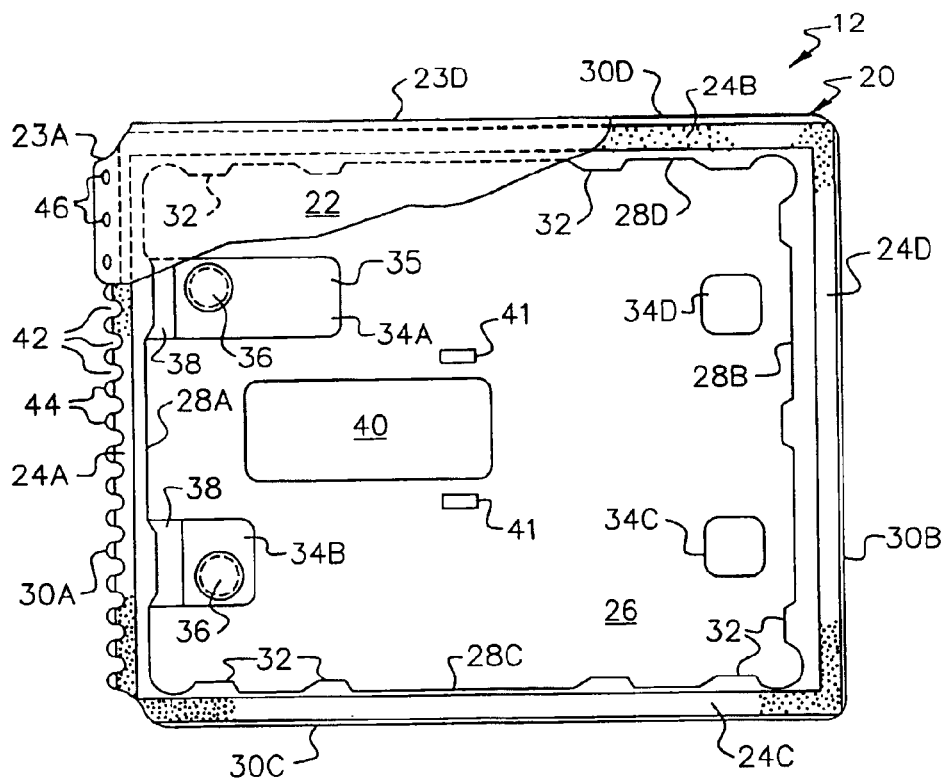
FIGS. 2 and 3 are respectively plan and side elevational views of a resealable cartridge incorporating the present invention.
Figure 3:
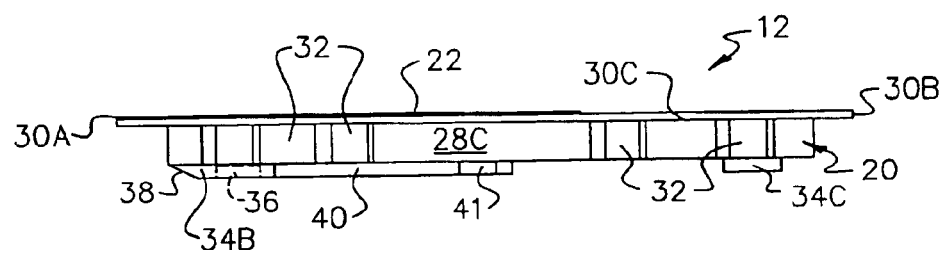

Resealable cartridge 12 can be described in greater detail with reference to FIGS. 2 and 3. As shown, cartridge 12 includes a optically opaque polymer film-receiving tray 20 and flexible, optically opaque polymer cover 22. Cover 22 is resealably mounted to tray 20 by adhesive coating 24A–24D. Other resealing techniques can be used such as magnetic strips. Tray 20 is preferably molded in one piece from a polymeric material.

Tray 20 is a relatively shallow member and includes a generally planar bottom wall 26, front wall 28A, rear wall 28B and side walls 28C and 28D. Lips 30A–30D extend outwardly from the upper edges of respective walls 28A–28D, and circumscribe a film access opening of tray 20. Inwardly projecting guides 32 are formed on walls 28A–28D to properly position sheets of film (not shown) within tray 20. Feet 34A–34D are formed into and extend downwardly from bottom wall 26 to support cartridge 12 within base 16 of laser imager 10. Bottom wall 26 also includes positioning recesses 36 which are tapered and extend into tray 20 from the bottom wall. Positioning recesses 36 are configured to receive positioning lugs extending from base 16. The positioning lugs secure and properly orient cartridge 12 within laser imager 10. In the embodiment shown, positioning recesses 36 are molded into feet 34A and 34B adjacent to front wall 28A. A media presence monitoring well 35 is also formed in bottom wall 26. Media presence monitoring sensors of imager 10 (not shown) extend into well 35 below the surface of bottom wall 26 when all film has been removed from tray 20.

Feet 34A and 34B (i.e., those adjacent to front wall 28A) also include ramp surfaces 38 which slope downwardly from the lower edge of the front wall to the bottom of the feet.

Ramp surfaces 38 guide feet 34A and 34B over the positioning lugs in imager base 16 as cartridge 12 is being loaded into the base. The embodiment of tray 20 illustrated in FIGS. 2 and 3 also includes a recess 40 in bottom wall 26 which forms a platform on the bottom exterior of tray 20. A pair of feet 41 are formed as releases in bottom wall 26 adjacent recess 40. Reinforcing ribs (not shown in FIGS. 2 and 3) can also be molded into bottom wall 26 and/or side walls 28A–28D to increase the rigidity of tray 20.

The forward most or leading edge of front lip 30A also includes a series of spaced cut-out sections 42. Cut-out sections 42 form a series of spaced projections 44 on the leading edge of lip 30A. Cut-out sections 42 and projections 44 cooperate with yet to be described aspects of cover 22 and opening/closing mechanism 18 to facilitate the opening and subsequent closing of cartridge 12.

Cover 22 is a flexible, photo-inert and optically opaque sheet of material sized to extend over the access opening of tray 20. Cover 22 has edges 23A–23D (only edges 23A and 23D are shown in FIG. 2) which extend between and mate with tray lips 30A–30D, respectively.

The front edge 23A of cover 22 extends over the tray cut-out sections 42, and includes elongated apertures 46 which are positioned over the cut-out sections when the cover is sealed onto tray 20. Apertures 46 facilitate the engagement of opening/closing mechanism 18 with cover 22 in a manner described below.

Figure 4:
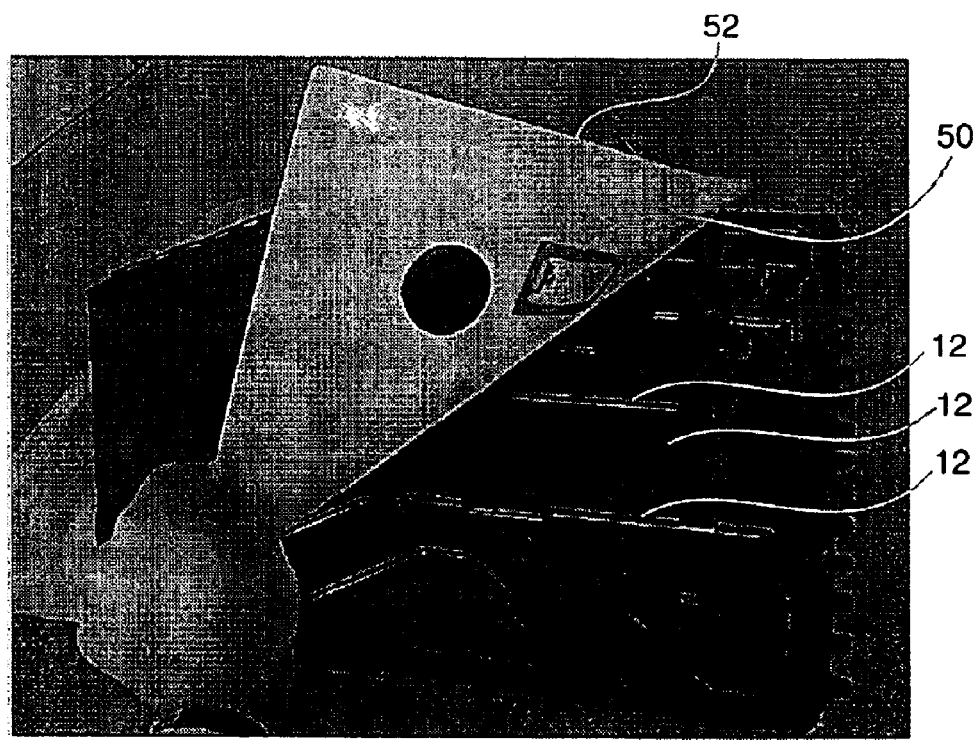
FIG. 4 is a perspective view of an embodiment of the present invention.

Cartridge 12 is provided with a stack of photosensitive sheet media, such as unexposed radiographic film used in laser imagers. The film may be processable by conventional wet processing techniques or by thermographic dry processing techniques. According to the present invention cartridge 12 has a radio frequency identification (RFID) transponder associated with it. As shown in FIG. 4, an inlay transponder 50 is mounted on the bottom of liner 52 facing the bottom wall of cartridge 12.

Figure 5:
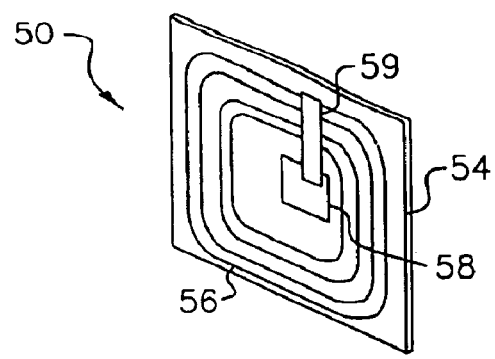
FIG. 5 is a diagrammatic view of a transponder, which can be used in the present invention.

Radio-frequency identification transponders are widely available in a variety of forms. Inlay transponders have a substantially flat shape. FIG. 5 shows an inlay transponder 50 having a flexible support sheet 54 carrying a planar flat coil antenna 56 and integrated circuit chip 58 having a non-volatile digital memory such as an EEPROM (Electrically Erasable Programmable Read-Only Memory). Stored in non-volatile memory are relevant encoded digital data. Sheet 54 is electrically insulating plastic and antenna 56 is a layer of conductive material deposited on sheet 54. Connectors 59 and necessary insulation are provided as deposited layers. Inlay transponders of this type are marketed by Texas Instrument Inc., Dallas, Tex. as Tag-it™ inlays. Transponders supplied from other sources may also be used. The transponder is interrogated by an RF signal from an external transceiver which is not in contact with the transponder and may be some distance from it. The transponder has a unique ID code which is transmitted to the transceiver upon interrogation. Data can be both written to and read from the non-volatile memory. In this embodiment other transponder configurations can be used in place thereof. For example, the transponder can be cylindrical.

Figure 6:
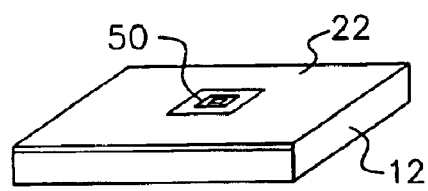
FIGS. 6–8 are diagrammatic views of other embodiments of the present invention.
Figure 7:
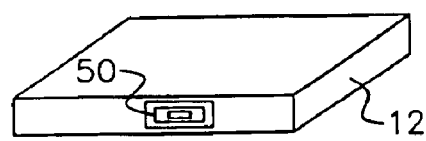
Figure 8:
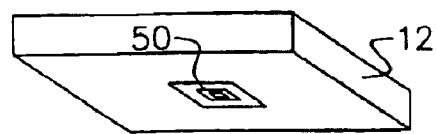

The transponder associated with cartridge 12 can be mounted in other areas thereof. FIG. 6 shows transponder 50 mounted on upper sheet 22. FIG. 7 shows transponder 50 mounted on the side of cartridge 12. FIG. 8 shows transponder 50 mounted on the outside surface of cartridge 12 can also be mounted on the inside surface of the bottom of the cartridge 12. It will be understood that transponder 50 can be mounted on cartridge 12 in any convenient area on the inside or outside thereof. Alternatively, the transponder can be an integral part of the cartridge.

Figure 9:
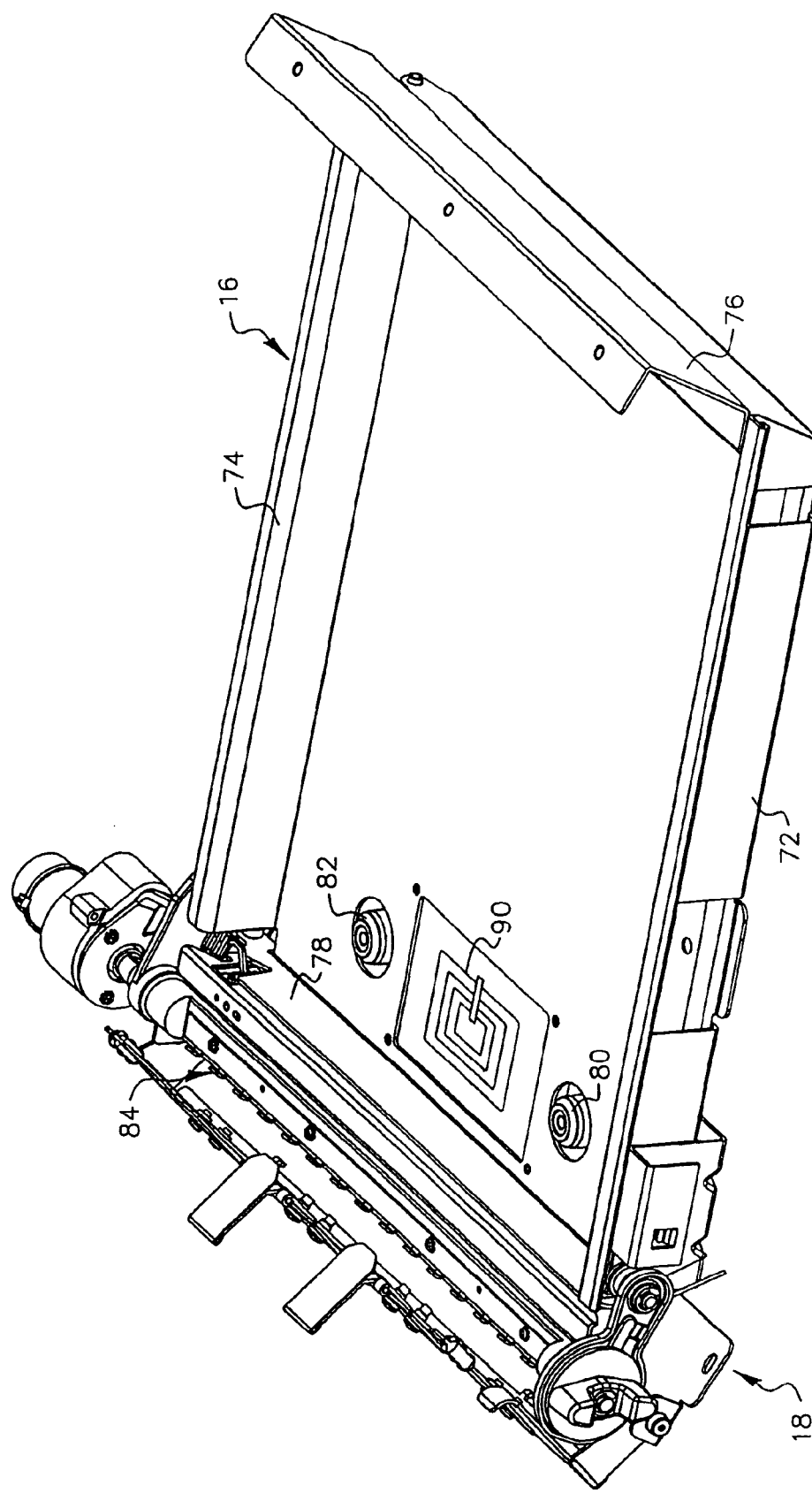
FIGS. 9–11 are perspective views of a cartridge receiving base with transceiver according to an aspect of the invention.
Figure 10:
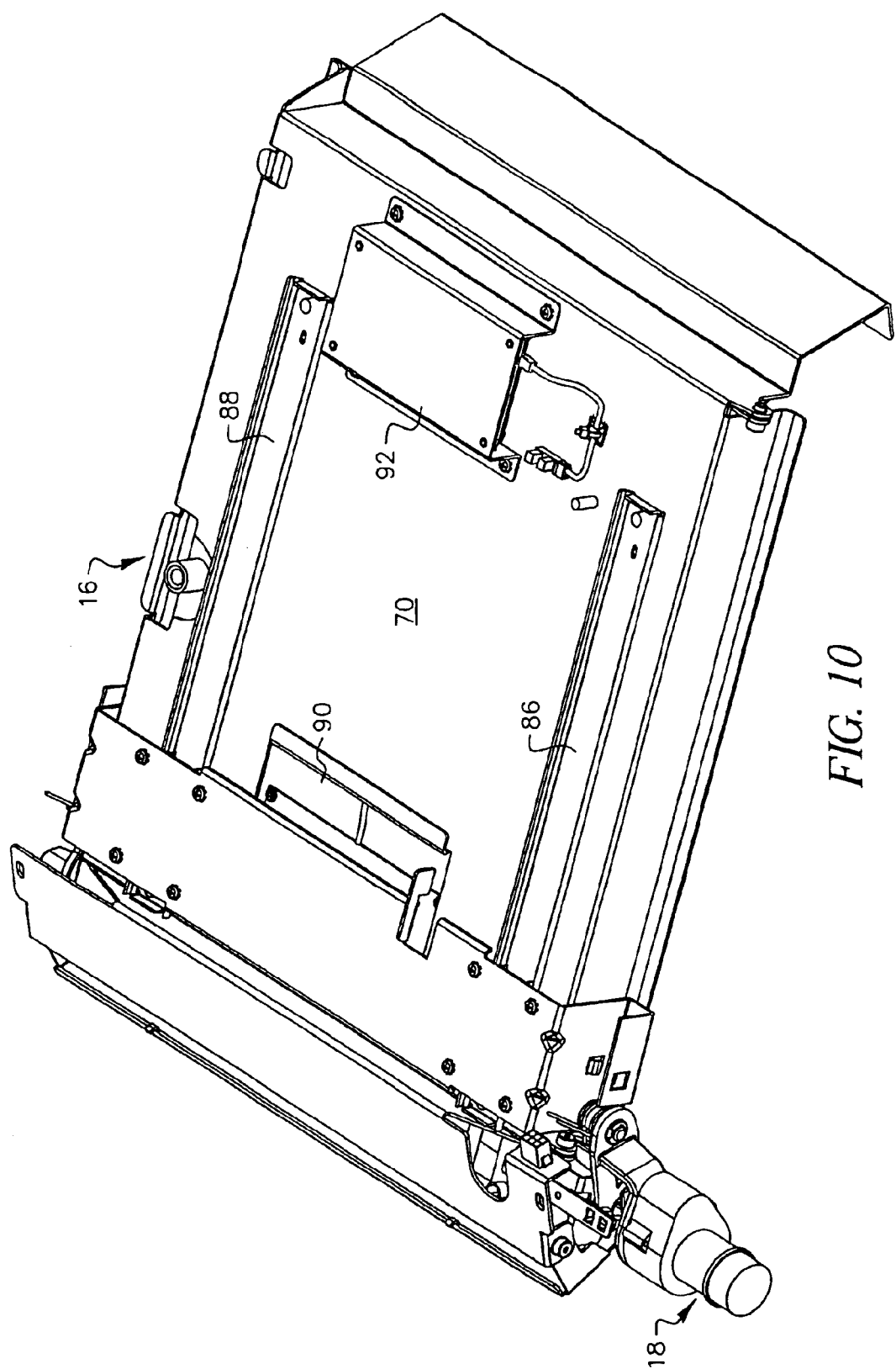
Figure 11:
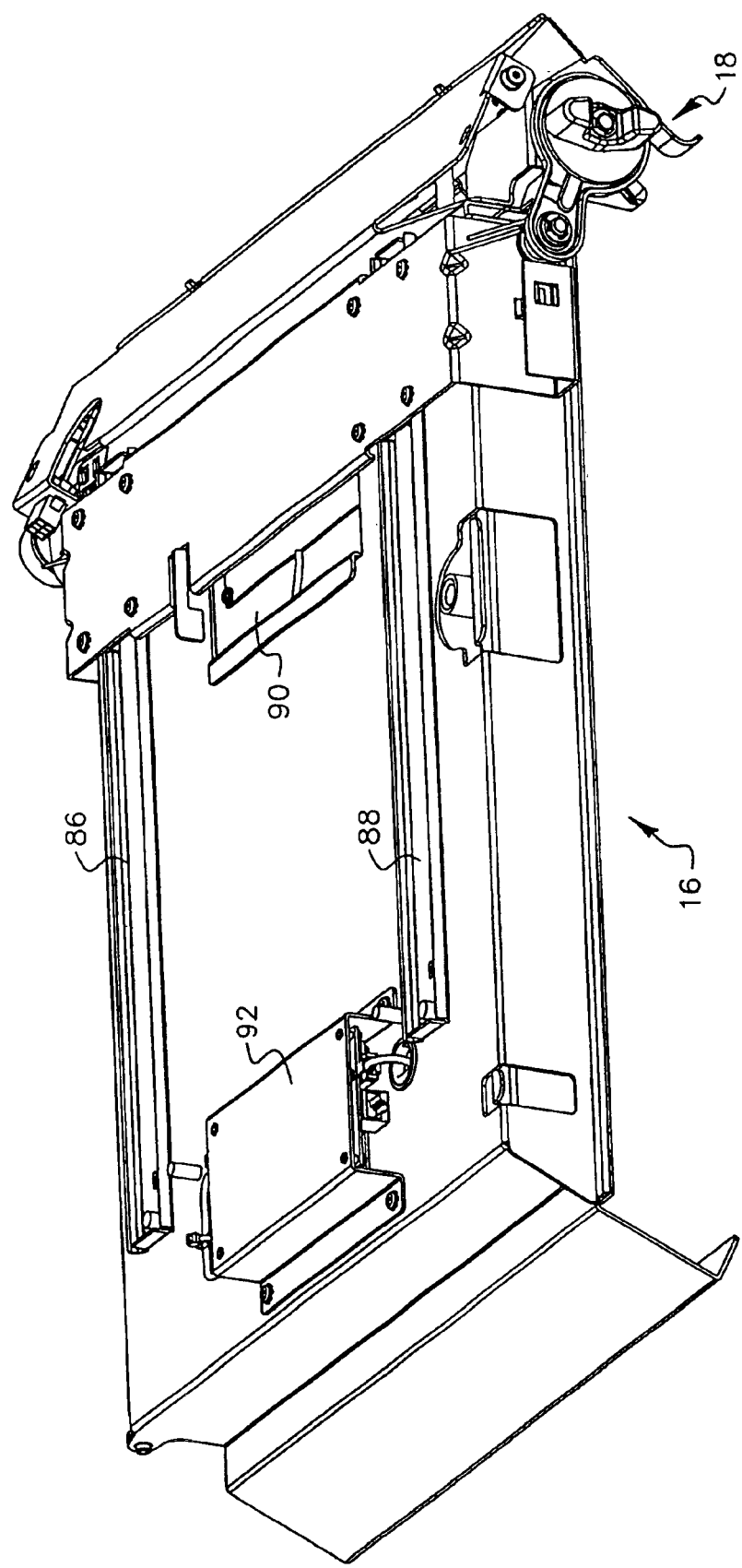

Referring now to FIGS. 9–11, there is shown cartridge receiving base 16 and opening and closing mechanism 18. Base 16 is mounted in imager 10 (FIG. 1). Base 16 has a bottom member 70 side members 72, 74, rear member 76, and front member 78. Lugs 80, 82 engage recess 36 of cartridge 12 to position cartridge 12 in base 16. Opening/closing mechanism 18 has a unit 84 which engages the apertures 46 of cover 22 to roll it back for removal of film sheets from cartridge 12. Mechanism 18 rides in tracks 86, 88. The operation of mechanism 18 is described in greater detail in U.S. Pat. No. 5,132,724, issued Jul. 21, 1992, inventors Lemberger et al., the contents of which are incorporated herein by reference and will not be repeated here.

The transceiver for communicating with transponder 50 includes an antenna 90 and read/write electronics 92 electrically connected to antenna 90. Antenna 90 is located in proximity to transponder 50 when cartridge 12 is positioned in base.

Figure 12:
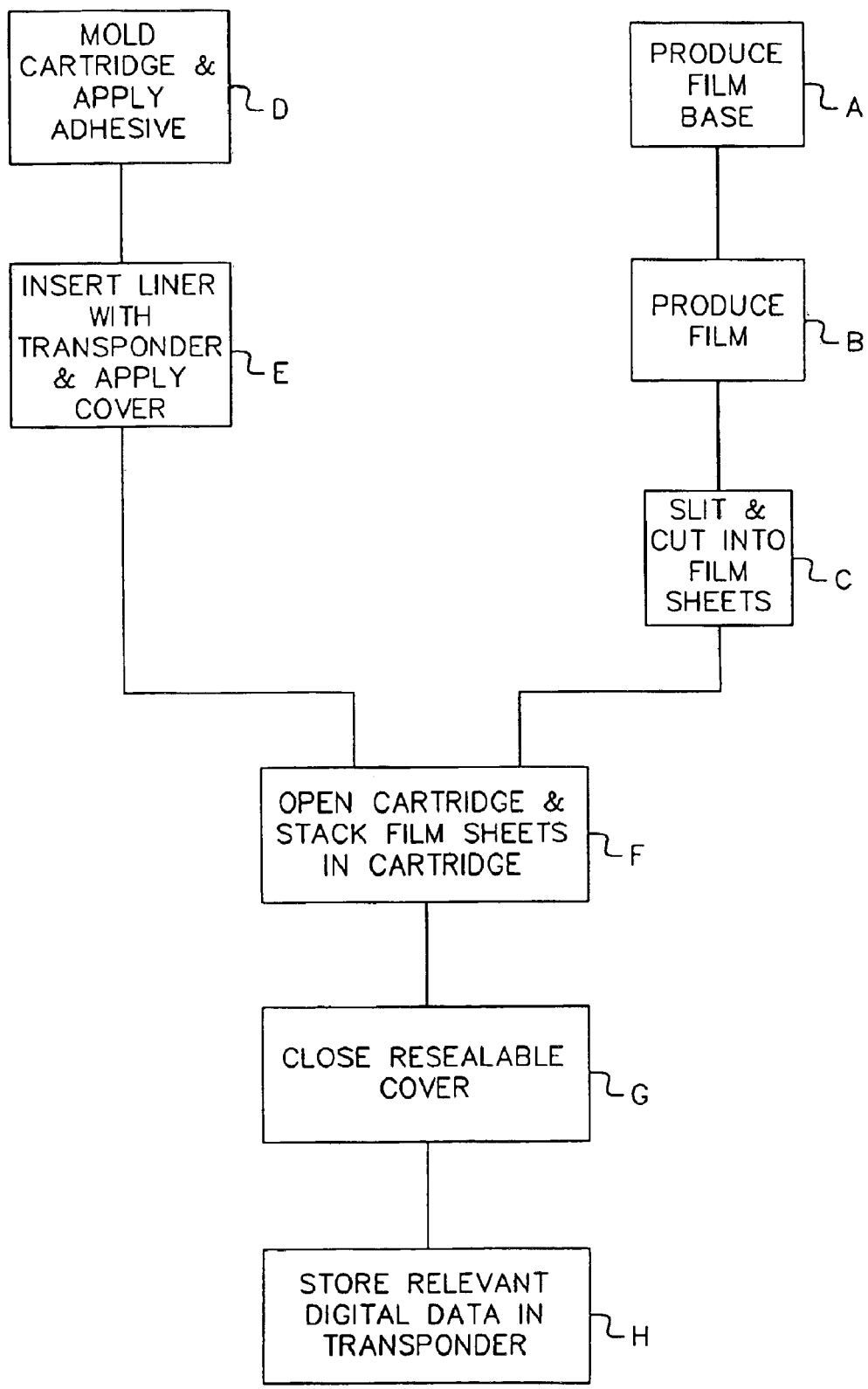
FIG. 12 is a block diagram of a cartridge/film manufacturing process.

FIG. 12 is a block diagram of an exemplary manufacturing process for making film cartridge 12. As shown, process A produces a wide web film base which is coated in process B to produce unexposed film. A large roll of wide film is then slit into narrower strips which are cut into sheets (process C). A five sided cartridge with an open top is molded in process D and adhesive added to the upper edges of the cartridge. A liner with transponder is inserted into the bottom of the cartridge and a resealable cover is applied in process E. In process F, the cartridge is opened and a stack of film sheets is inserted into the cartridge on top of the insert. In process G, the resealable cover is closed. In process H, one or more film or cartridge processes or other relevant digital data are stored in the transponder.

Figure 13:
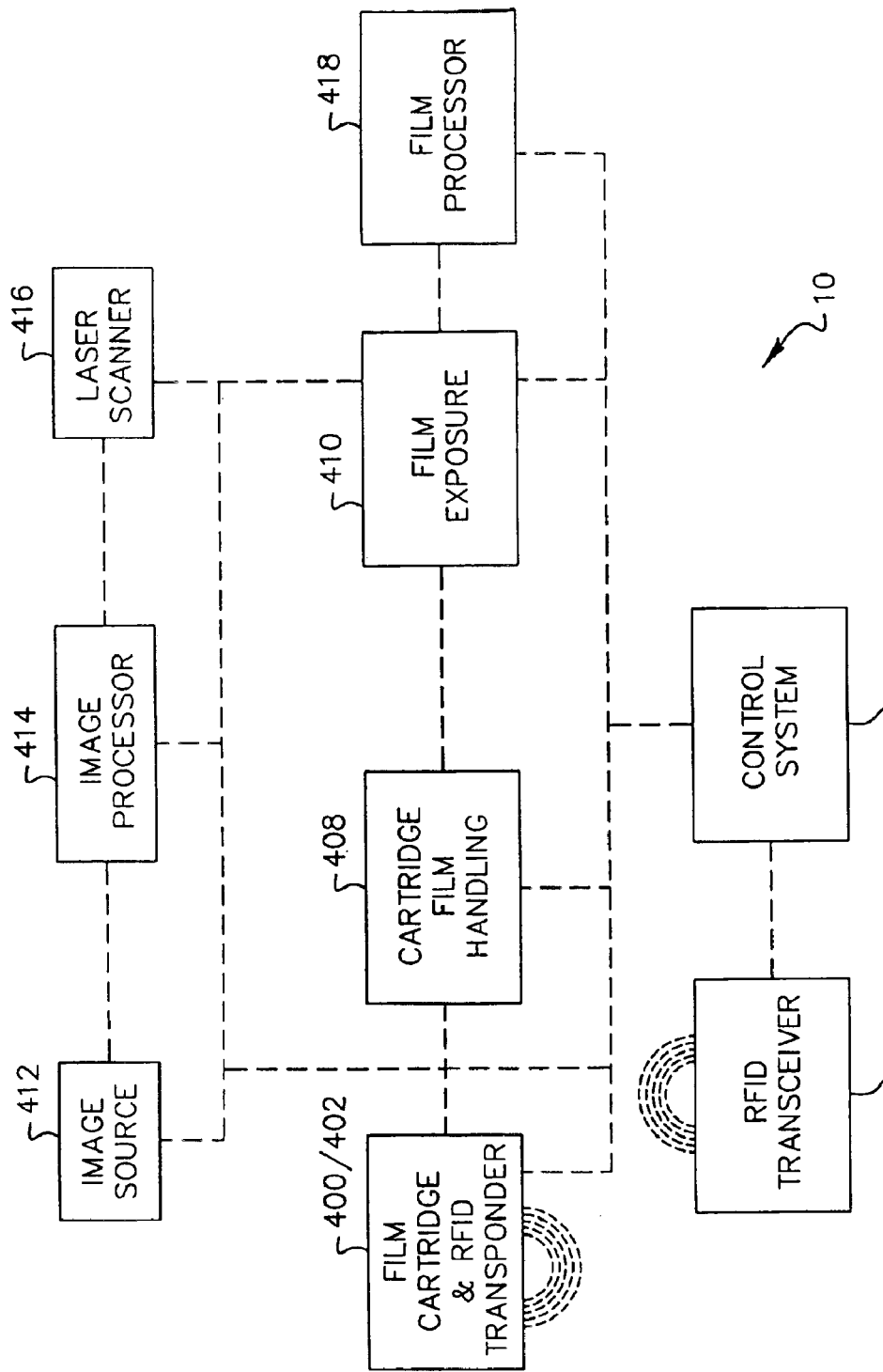
FIG. 13 is a general block diagram of a radiographic laser imager.

Referring to FIG. 13, there is shown a block diagram of imager 10. A film cartridge 400 containing unexposed radiographic film and having a transponder 402 is loaded into imager 10. RFID transponder 402 is interrogated by RFID transceiver 404 under the control of control system 406. Cartridge/Film Handling system 408, opens the film cartridge, removes a sheet of film, and transports it to Film Exposure Station 410. Image Source 412, such as a digital radiographic image storage, transmits an image to be reproduced to Image Processor 414, where the image can be processed for various parameters including ones which have been derived from data supplied by RFID transponder 402. Such data can include film size, film sensitometry, film age, etc. The processed image is reproduced by Laser Scanner 416 on a film sheet located at Film Exposure Station 410. The exposed film is then processed by Film Processor 418 which can be a wet process film processor or a dry film processor. An exemplary laser imager for use with heat processable dry film is described in U.S. Pat. No. 6,007,971, issued Dec. 28, 1999, inventors Star et al.

According to the invention the cartridge transponder can store one or more of the following types of relevant digital data, among others.

1. Unique transponder ID number
2. Cartridge ID number
3. Film type, lot number, all manufacturing machines or processes that film saw (e.g., those associated with processes A, B, and C of FIG. 12).

4. Film expiration date

5. Film size and initial number of film sheets in cartridge

6. All manufacturing machines or processes that cartridge saw (e.g., those associated with processes D, E, F, G of FIG. 12)

7. Messages for customers, sales or service

8. Upgrade software for the laser imager

According to a further feature of the invention, the laser imager transceiver can transmit one or more of the following types of data to the film cartridge transponder after installation in the laser imager.

1. Number of film sheets remaining in the cartridge.

2. Any measured laser imager parameter such as film calibration, image processing look up tables, motor speeds, temperature, errors, transfer functions, laser imager ID number, imager film usage, density patch tracking for Automatic Image Quality Control.

3. Any information relating to recycling of the cartridge such as: number of times recycled, date of recycling, time from last recycle, error codes that can prevent cartridge from being reused.

4. Laser imager failures, such as: sheet film jams, optic failure, communication problems, recalibration.

5. Times to scheduled service, preventive maintenance, error fix, film supply.

6. Codes to facilitate auditing of film, cartridge, customer, imager.

Although the present invention is described as associated with a cartridge containing sheet media, it will be understood that the RFID transponder can be used with other types of sheet media packaging, such as the flexible packaging disclosed in U.S. Pat. No. 5,973,768, issued Oct. 26, 1999, inventors Mazion et al., the contents of which are incorporated herein by reference.

Figure 14:
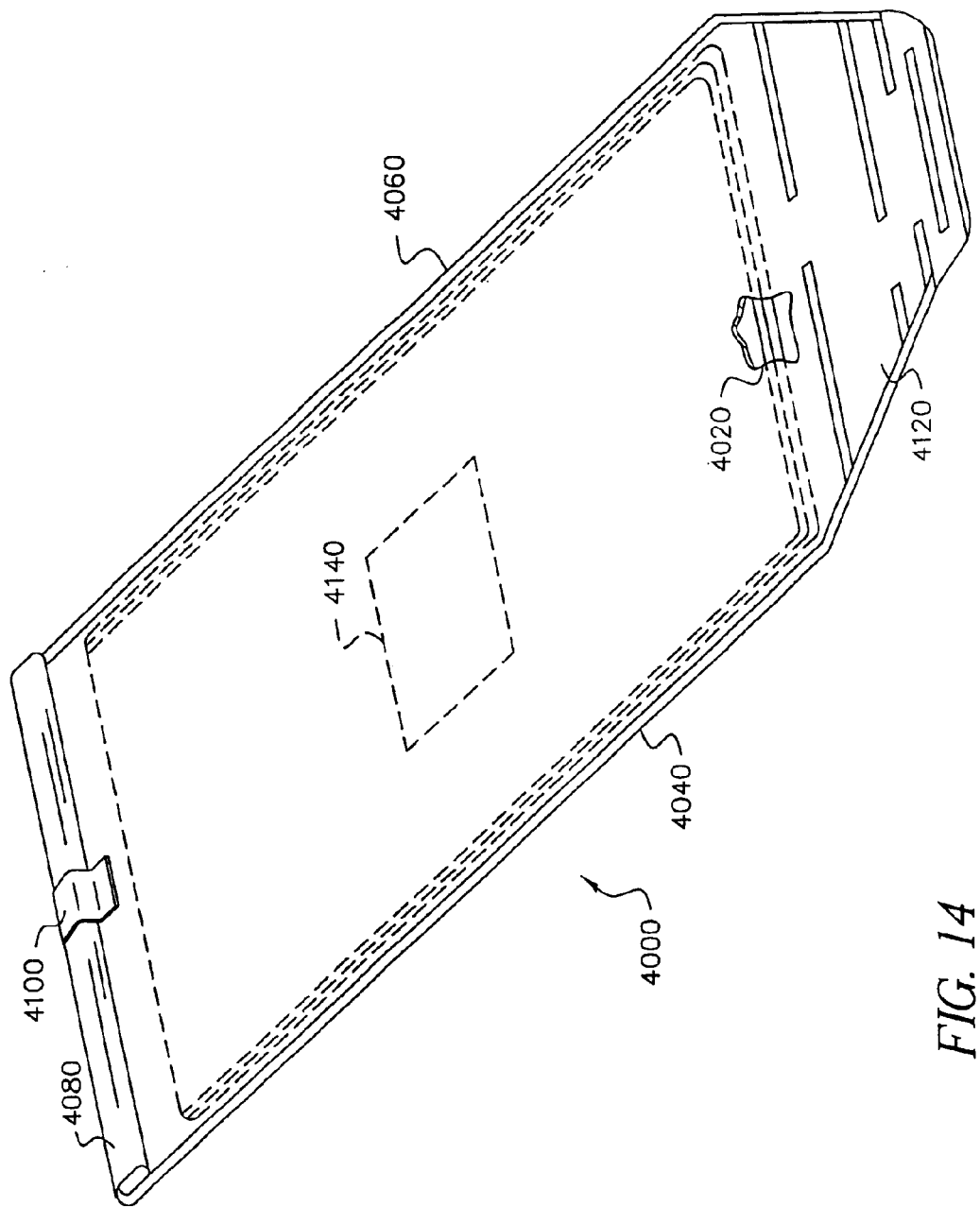
FIGS. 14 and 15 are diagrammatic views of other embodiments of the present invention.

As shown in FIG. 14, flexible packaging 4000 includes a light tight enclosure for a stack of light sensitive media sheets 4020. Packaging 4000 is made of a bag having sides 4040, 4060, rolled up end 4080 secured by tape 4100 and tapered end 4120. Packaging 4000 can be inserted in a light tight sheet media supply in a laser printer and removed in the printer by mechanical means to leave the stack of media sheets 4020 in the printer supply. (Reference is made to U.S. Pat. No. 5,765,091, issued Jun. 9, 1998, inventors Kovach et al., for an exemplary apparatus in which the packaging 4000 may be used).

According to a feature of the present invention, RFID transponder 4140 is associated with packaging 4000. Transponder 4140 stores relevant digital data as further explained above. The apparatus utilizing packaging 4000 includes a transceiver for communicating with the transponder associated with the packaging as further explained above.

Figure 15:
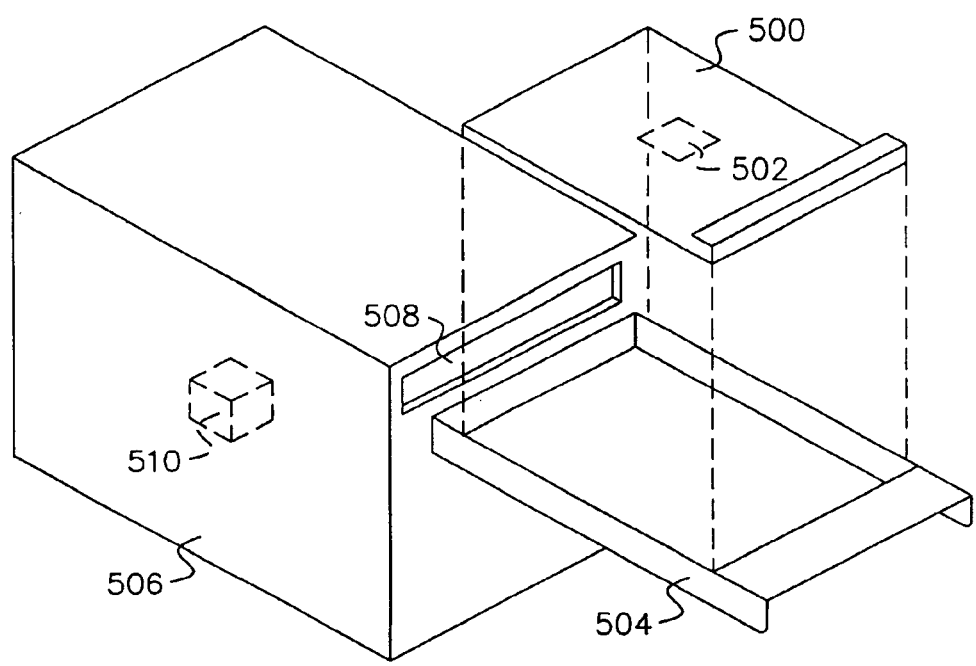

Instead of associating the RFID transponder with a sheet media cartridge of other packaging containing the sheet media, another feature of the present invention illustrated in FIG. 15, involves placing a removable transponder in apparatus utilizing sheet media, in proximity to a transceiver located in the apparatus. For example, as shown, an insert 500 having transponder 502 associated therewith, is inserted in sheet media supply drawer 504. Sheet media are stacked on insert 500 in drawer 504. Drawer 504 is inserted into sheet media utilization apparatus 506 through slot 508. Apparatus 506 includes transceiver 510 which communicates with transponder 502. Other techniques for providing transponder 502 will be apparent to those skilled in the art.

It will also be understood that other types of sheet media can be used in association with the transponder of the present invention. Thus, sheet media used in other printing systems such as ink jet, thermal, dye transfer, electrographic, lithographic, ink contact, or the like are considered within the scope of the present invention.

The invention has been described in detail with particular reference to certain preferred embodiments thereof, but it will be understood that variations and modifications can be effected within the spirit and scope of the invention.

PARTS LIST 10 digital imager
12 film cartridge
14 sheet film
16 cartridge-receiving base
18 opening/closing mechanism
20 tray
22 polymer cover
23A–23D edges
24A–24D adhesive coating
26 planar bottom walls
28A–28D walls
30A–30D lips
32 guides
34A–34D feet
35 well
36 recess
38 ramp surface
40 recess
41 feet
42 cut-out sections
44 projections
46 apertures
50 transponder
52 liner
54 support sheet
56 coil antenna
58 circuit chip
59 connectors
70 bottom number
72–74 side members
76 rear member
78 front member
80–82 lugs
84 unit
86–88 tracks
90 antenna
92 electronics
110 exposure station
118 film processor
201 enclosure
202 upper chamber
204 lower chamber
208 scanning module
210 electronic module
211 power supply
228 suction fed mechanism
230 staging area
232 film staging mechanism
234 center roller
236–238 idler rollers
244 film platen
246 film feed slot
248 film alignment device
264 densitometer
266 openable cover 280 output tray
310 thermal processor
314 heated member
316 guide member
402 transponder
404 transceiver
406 control system
408 cartridge/film handling system
410 film exposure station
412 image source
414 image processor
416 laser scanner
500 insert
502 transponder
504 drawer
506 apparatus
508 slot
510 transceiver
4000 flexible packaging
4020 media sheets
4040–4060 sides
4080 end
4100 tape
4120 end
4140 transponder

What is claimed is:

1. A sheet media package system comprising:
a support member which includes a supply area for holding a plurality of sheet media; and
a radio-frequency identification transponder disposed inside the support member and which can be communicated with while the sheet media are removed from the supply area, without physical contact with the transponder, and which stores relevant digital data, wherein the transponder remains inside the support member until removal of all of the sheet media.

2. The sheet media package system of claim 1, wherein the transponder is disposed on the support member beneath the plurality of sheet media.

3. The sheet media package system of claim 1, wherein the transponder is disposed on the side of the support member.

4. The sheet media package system of claim 1, wherein the transponder is disposed on a removable support disposed in the supply area beneath the plurality of sheet media.

5. The sheet media package system of claim 1, wherein the transponder is disposed on top of the plurality of sheet media.

6. The sheet media package system of claim 1, wherein the transponder stores digital data representing one or more of the following: media type information, media sheet count information, media performance information, media sensitometric information, messages or customers, sales or service personnel, upgrade software for the apparatus, software parameters for the apparatus, packaging recycle data, apparatus performance optimization information, or machine error information.

7. The sheet media package system of claim 1, wherein the digital memory is a read-only or a read/write memory.

8. The sheet media package system of claim 1, wherein the package system is a light-tight flexible package and wherein the transponder is disposed on the inside of the light-tight package.

9. The sheet media package system of claim 1, wherein the support member is a cartridge, and the transponder stores digital data representing one or more of the following: cartridge manufacturing history, cartridge recycling data, cartridge error codes.

10. A sheet media package system comprising:
a package which holds a plurality of sheet media defining a stack; and
a radio-frequency identification transponder disposed inside the package on a support and which can be communicated with while the sheet media are individually removed from the stack, without physical contact with the transponder, and which stores relevant digital data, wherein the transponder remains disposed on the support until all the sheet media are removed from the stack.

11. The sheet media package system of claim 10, wherein the support is located beneath the stack, and the support remains beneath the stack until all the sheet media are removed from the stack.

12. The sheet media package system of claim 10, wherein the support is located within or on top of the stack, and the support remains within or on top of the stack until all the sheet media are removed from the stack.

13. The sheet media package system of claim 10, wherein the package is light-tight.

14. The sheet media package system of claim 10, wherein the support is a sheet.

15. A sheet media package system comprising:
a plurality of sheet media;
a radio-frequency identification transponder disposed on a support and which stores relevant digital data, the support and the plurality of sheet media defining a stack;
a package having a holding area for holding the stack and an opening through which to remove the stack from the enclosure; and
a supply drawer having a supply area adapted to receive the stack when removed from the package, an egress through which the plurality of sheet media can be individually removed from the supply drawer, and a transceiver which can communicate with the transponder without physical contact with the transponder while the sheet media is individually removed from the supply drawer through the egress, and wherein the support with the transponder remains in the supply area until removal of all the sheet media from the supply drawer.

16. A sheet media package system comprising:
a plurality of sheet media;
a support member, the plurality of sheet media and the support member defining a stack;
a package which holds the stack and has an opening through which to remove the stack from the package; and
radio-frequency identification transponder disposed on the support member which stores relevant digital data and which can be communicated with while the sheet media are being individually removed from the stack, without physical contact with the transponder, when the stack is removed from the enclosure, wherein said transponder on the support member remains disposed within said package beneath the plurality of sheet media until all the sheet media is removed from the stack.

17. The sheet media package system of claim 16, wherein the transponder is disposed beneath the plurality of sheet media.

18. The sheet media package system of claim 16, wherein the transponder is disposed on a side of the support member.

19. A method of providing sheet media from a supply area, comprising the steps of:

providing a radio-frequency identification transponder on a support, the transponder being adapted to store relevant digital data;

providing a transceiver which can communicate with the transponder, without physical contact with the transponder and providing a sheet media supply drawer having an op opening through which sheet media can be individually removed from a supply area in the supply drawer, the supply area being adapted to receive the support with the transponder such that the transponder can communicate with the transceiver while the sheet media are individually removed from the supply area and the support remains in the supply area until removal of all the sheet media.

20. A method of providing sheet media from a supply area, comprising the steps of:

providing a radio-frequency identification transponder on a support, the transponder being adapted to store relevant digital data;

providing a transceiver which can communicate with the transponder;

providing a supply drawer having an opening through which sheet media can be individually removed from a supply area disposed within the supply drawer, the supply drawer configured to receive the support and the sheet media in the supply area of the supply drawer such that the transponder can communicate with the transceiver without physical contact with the transponder;

allowing communication of the transponder and the transceiver while the sheet media are being individually removed from the supply area; and maintaining the support with the transponder in the supply area until removal of all the plurality of sheet media from the supply drawer.

21. A method of providing sheet media, comprising the steps providing a sheet media package system comprising:

(a) a plurality of sheet media;

(b) a radio-frequency identification transponder disposed on a sheet support and which stores relevant digital data, the support the plurality of sheet media defining a stack;

(c) a package having a supply area for holding the stack including the support with the transponder and an opening through which to remove the stack from the package; and enabling the sheet media package system to communicate with a transceiver disposed in a supply drawer when the stack is removed from the package and disposed in the supply drawer whereby the support with the transponder does not physically contact the transceiver and remain in the supply drawer until removal of all the sheet media from the stack.

* * * * *